United States Patent
Mushabac et al.

[19]
[11] Patent Number: 6,038,780
[45] Date of Patent: Mar. 21, 2000

[54] REMOTE SENSOR APPARATUS AND METHOD

[75] Inventors: David R. Mushabac, Brooklyn, N.Y.; Stanislaw A. Policht, Closter, N.J.

[73] Assignee: Dentrac Corp., Brooklyn, N.Y.

[21] Appl. No.: 08/927,546

[22] Filed: Sep. 6, 1997

Related U.S. Application Data

[60] Provisional application No. 60/025,560, Sep. 6, 1996.

[51] Int. Cl.[7] .................................................. A61B 5/107
[52] U.S. Cl. ................................. 33/512; 33/25.1; 33/551
[58] Field of Search .............................. 33/23.01, 23.09, 33/25.1, 551, 553, 554, 556, 511, 512, 513, 514; 364/413.13, 413.28, 560, 564; 433/72, 215

[56] References Cited

U.S. PATENT DOCUMENTS

| | | | |
|---|---|---|---|
| 733,321 | 7/1903 | Griswold | 33/513 |
| 1,082,052 | 12/1913 | Strang | 33/513 |
| 3,100,344 | 8/1963 | Sharp | 33/23.01 |
| 3,936,942 | 2/1976 | Belew et al. | 33/25.1 |
| 5,257,184 | 10/1993 | Mushabac | 433/72 |
| 5,291,901 | 3/1994 | Graf | 33/512 |
| 5,562,448 | 10/1996 | Mushabac | 433/215 |

*Primary Examiner*—G. Bradley Bennett
*Attorney, Agent, or Firm*—Don Halgren

[57] ABSTRACT

The present invention comprises an arrangement for the remote sensing and recordation of information about a body component. The arrangement includes a stylus held within a support head. The support head has an electrode therein for the detection and recordation of stylus contact with a body component. A plurality of parallelogram linkages articulably support the stylus. The linkages have a first or input end and a second or output end. A motion tracking generator is attached to the output end of linkages. A sensor is arranged to receive and record signals from the tracking generator in a plurality of orthogonal planes, so as to permit the generation and recordation of contours, location and domain of the body component being sensed by the stylus.

7 Claims, 4 Drawing Sheets

REMOTE SENSOR APPARATUS AND METHOD

BACKGROUND OF THE INVENTION

1. Field of the Invention

The present invention relates to a method and a system for sensing and mapping a body component, and more particularly, for mapping dental structures. This Application claims the benefit of U.S. Provisional Application Ser. No. 60/025,560 filed Sep. 06, 1996.

2. Prior Art

The remote sensing and mapping of remote components is desirable in the medical field, and particularly so in the dental field. This would permit the treatment, replacement, and resurfacing of body elements, if such tracking and sensing were available. Such remote sensing is desirable in the dental field, for the manufacture of crowns and tooth restoration.

Some devices are shown in the following patents, such as U.S. Pat. No. 5,017,139 to Mushabac, entitled "Mechanical support for hand-held dental/medical instrument"; U.S. Pat. No. 5,224,049 to Mushabac entitled "Method, system and mold assembly for use in preparing a dental prosthesis"; U.S. Pat. No. 5,257,184 to Mushabac, entitled "Method and apparatus with multiple data input stylii for collecting curvilinear contour data"; U.S. Pat. No. 5,343,391 to Mushabac, entitled "Device for obtaining three dimensional contoured data and for operating on a patient and related method"; U.S. Pat. No. 5,347,454 to Mushabac, entitled "Method, system and mold assembly for use in preparing a dental restoration"; U.S. Pat. No. 5,448,472 to Mushabac entitled "Method using reference indicia on tape attached to mouth surface to obtain a three dimensional contour data"; U.S. Pat. No. 5,545,039 to Mushabac entitled "Method and apparatus for preparing tooth or modifying dental restoration"; U.S. Pat. No. 5,562,448 to Mushabac entitled "Method for facilitating dental diagnosis and treatment"; and U.S. Pat. No. 5,569,578 to Mushabac entitled "Method and apparatus for affecting change in shape of pre-existing object". Each of the foregoing Mucabac Patents are incorporated herein by reference, in their entireties.

It is an object of the present invention, to provide a remote sensing apparatus and method which further improves upon the prior art.

It is yet a further object of the present invention, to provide a remote sensing apparatus which is useful for sensing human body components for the medical field.

BRIEF SUMMARY OF THE INVENTION

The present invention comprises a method and a system for the remote sensing of a body component by a hand held moveable stylus which permits the simultaneous recordation of a plurality of signals to map and track the shape, size, and contour of a component, such as a body organ, i.e., a tooth, bone, or the like. The system includes a stylus, which is an elongated pin pivotably supported along its mid portion, in a head. The distal end of the stylus has a first radius. The second end of the stylus is movably supported within a hemispherically shaped electrode. A compression spring maintains a bias on the stylus, yet permits the proximal end of the stylus to pivot and strike the electrode during a swinging or pivoting motion of the stylus or a longitudinal motion of the stylus. When such contact is made, a signal is sent through a proper circuit for recordation as to the time and the location of such contact.

The stylus and head are disposed on the distal end of a freely swingable first arm. The first arm is supported on a main shaft. The first arm is permitted to swing or pivot in any direction or angle because the main shaft is rotatably supported in a bearing disposed on the distal end of a holding arm. The holding arm is supported in a bearing on the distal end of a second arm. The second arm is supported by a bearing having a vertically disposed axis. The vertically disposed axis holding the second arm is always in vertical alignment with the distal end of the stylus. The second arm is connected to an arrangement of parallelogram linkages, forming a 3D pantograph. The pantograph is anchored to a support stand or to ground. One end of the pantograph linkage is attached to a laser beam generator.

The laser beam generator has an output, a proportion of which comprises a reflected beam and a straight exit beam. The exit beam and the reflected beam are directed towards X, Y, and Z planes of a sensor apparatus. Such sensor apparatus may be seen in the aforementioned patents, incorporated by reference herein. Such a sensor is similar to that manufactured by EG&G called an Amorphous Silicon Screen Sensor.

The second arm, connected to the first vertical linkage, comprises one side of the first parallelogram. The first vertical linkage has an upper bearing and a lower bearing thereattached. An upper first horizontal linkage and a lower first horizontal linkage are attached to upper and lower portions of the first vertical linkage by a bearing which permits the upper horizontal linkage and the lower horizontal linkage to move in a vertical plane. A second vertical linkage completes the first rectangle comprising the pantograph. The second vertical linkage has a bearing on its uppermost end, in arrangement with the first horizontal linkage and the lower horizontal linkage. The second vertical linkage also has an upper and a lower bearing permitting rotation of that vertical linkage about the vertical axis. A second parallelogram comprised of a second primary vertical linkage and a second secondary vertical linkage, each second primary vertical linkage and second secondary vertical linkage are connected by parallel upper and lower linkages. The first parallelogram and the second parallelogram are each connected by a pair of upper and lower linkages, one of which extends to a third vertical linkage for ground support.

The second primary vertical linkage has an upper end onto which a laser beam generator is mounted. The laser beam generator has a beam reflector thereon. The laser beam passes partially through the reflector and part of the beam is reflected by the reflector. The axis of rotation of the second primary vertical linkage is coaxial with the reflected laser beam, reflected from the reflector. The reflected laser beam strikes the aforementioned sensor in the plane defined by the XY axes thereof. The exit beam passing through the reflector strikes the sensor defined by the ZX axes.

The split laser beam output permits simultaneous tracking by the sensors, of the motion by the stylus. When the stylus is in contact with an object, such occurance and location is recorded by virtue of the electrode input generated by its contact with the stylus head. The spherical contact area of the head is twice the radius of the stylus. By virtue of the relative sizes of the two parallelagram connected as the pantograph assembly, there is a proportion two to one ratio of motion to tracking dimension recorded by the sensor. The location of the distalmost tip of the stylus is always in axial alignment with the first vertical link of the first parallelogram, no matter what angle the stylus head is turned, rotated, or swung in, such orientation is always maintained. The reflected laser beam is always in axial alignment with the second primary vertical link of the second parallelagram. Thus the multiplication factor between the two parallelagrams in their pantograph linkages permits an accurate tracking of location and data through a proper control circuit connected to the sensors. By the combination of signals from the stylus, as to when contact is made with an article or object and its recordation through the circuit from the electrode in the head, in conjunction with the signals generated by the laser beam, an accurate domain may be mapped of a body component or the like.

The invention thus comprises an arrangement for the remote sensing and recordation of information of a body component, comprising a stylus held within a support head, the support head having an electrode therein for the detection and recordation of stylus contact with a body component; a plurality of parallelogram linkages articulably supporting the stylus, the linkages having a first or input end and a second or output end; a motion tracking generator attached to the output end of linkages; and a sensor arranged to receive and record signals from the tracking generator in a plurality of orthogonal planes, so as to permit the generation and recordation of contours, location and domain of the body component being sensed by the stylus. The tracking generator comprises a laser beam generator. The paralellogram linkages includes a first linkage having an axis which is in axial alignment with the distal end of the stylus. The parallelogram linkages has an end linkage with an axis which is in coaxial alignment with the axis of a beam generated by the laser generator.

The invention includes a method of sensing and recordation of the contours and location of a body component using a plurality of pantograph linkages having a movable stylus an an arm at a first end of the linkages and a signal generator at a linkage at a second end of the linkages, comprising the steps of: moving the stylus about and against the body component being sensed; recording the location of the stylus during touching contact of the stylus with the body component; and generating an output signal by the signal generator attached to the second end of linkage, to track and permit the recording of the location of the stylus as the stylus is moved about the body component. The method includes the steps of receiving the output signal onto an XYZ plane sensor to permit the receipt and recordation of the output signals; splitting the output signal onto a plurality of receiving sensors screens to permit separation and identifigation of the signal.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
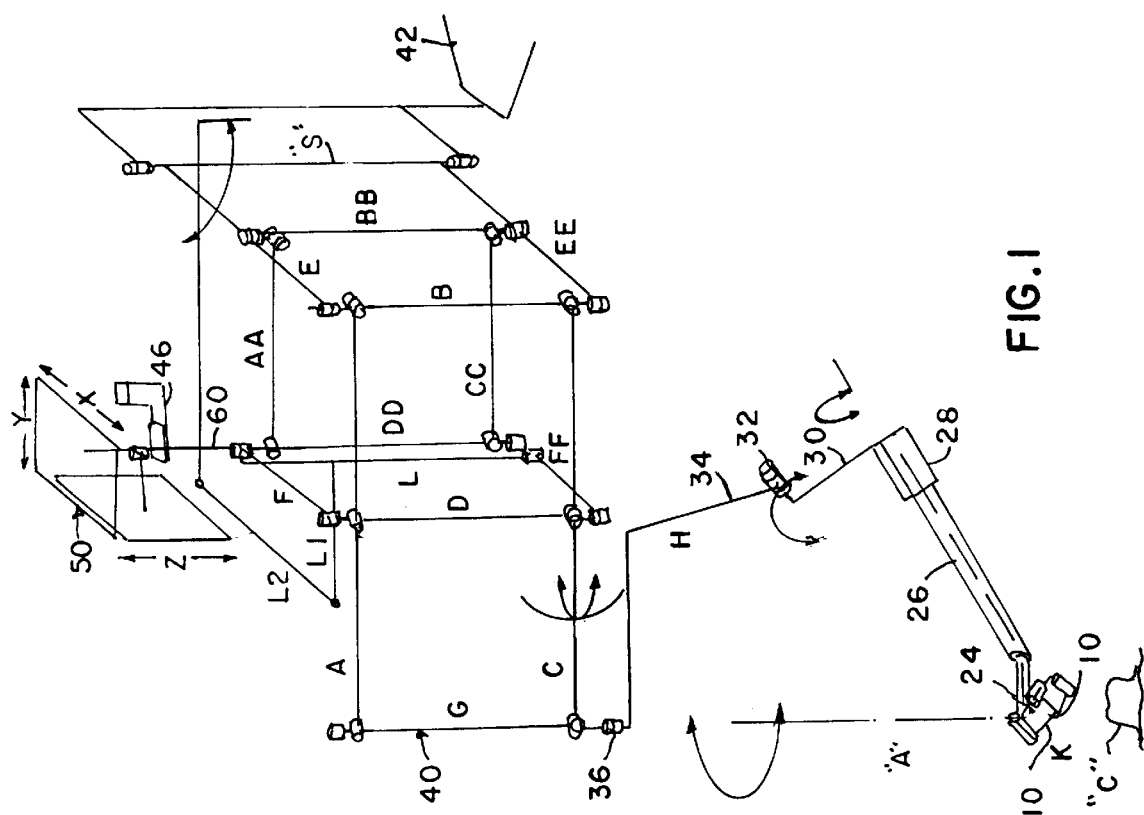
FIG. 1 is a schematically represented isometric view of the sensor and pantograph constructed according to the principles of the present invention.
Figure 2:
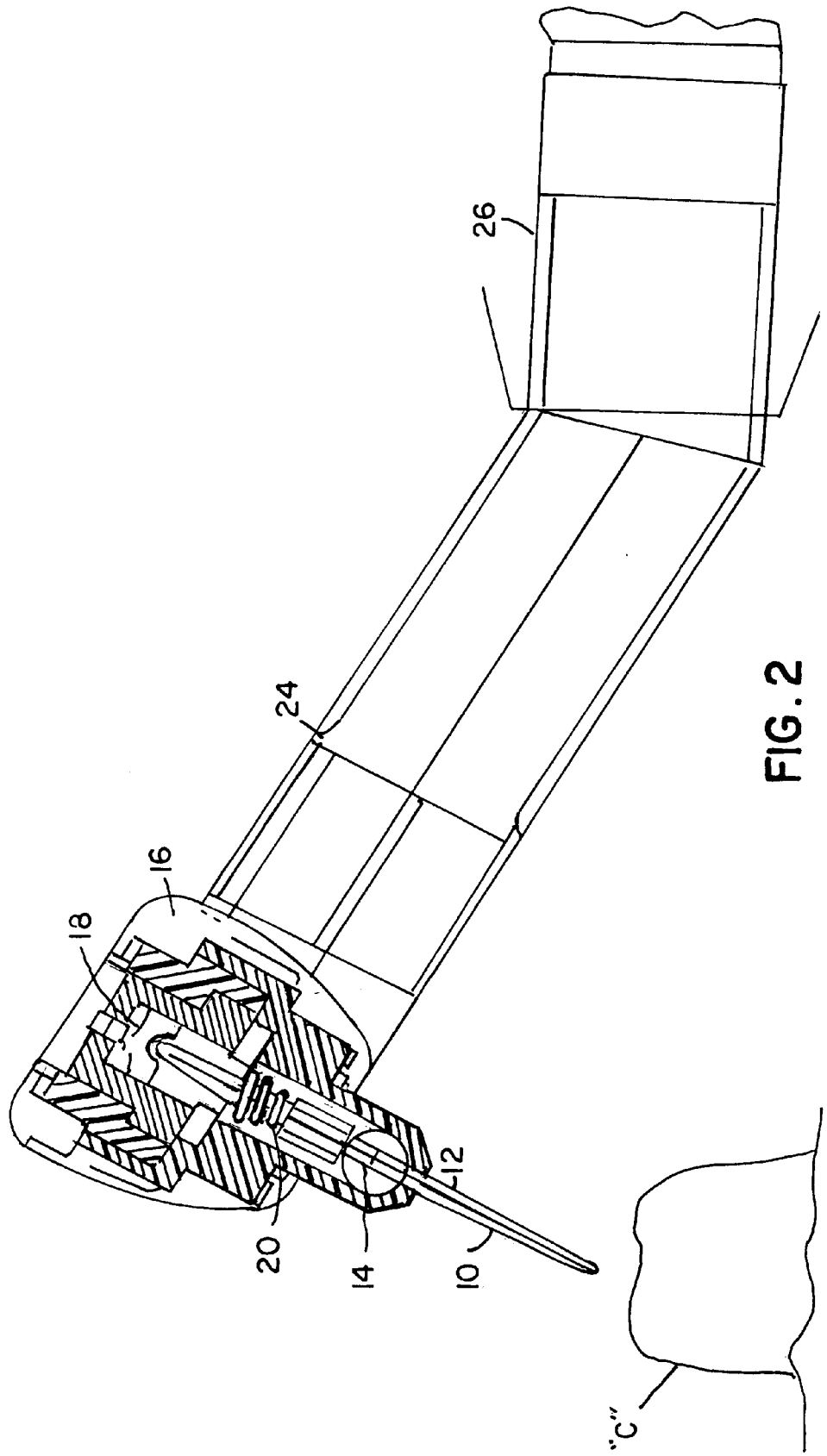
FIG. 2 is a side elevational view of the stylus and head in section, of the present invention.
Figure 3:
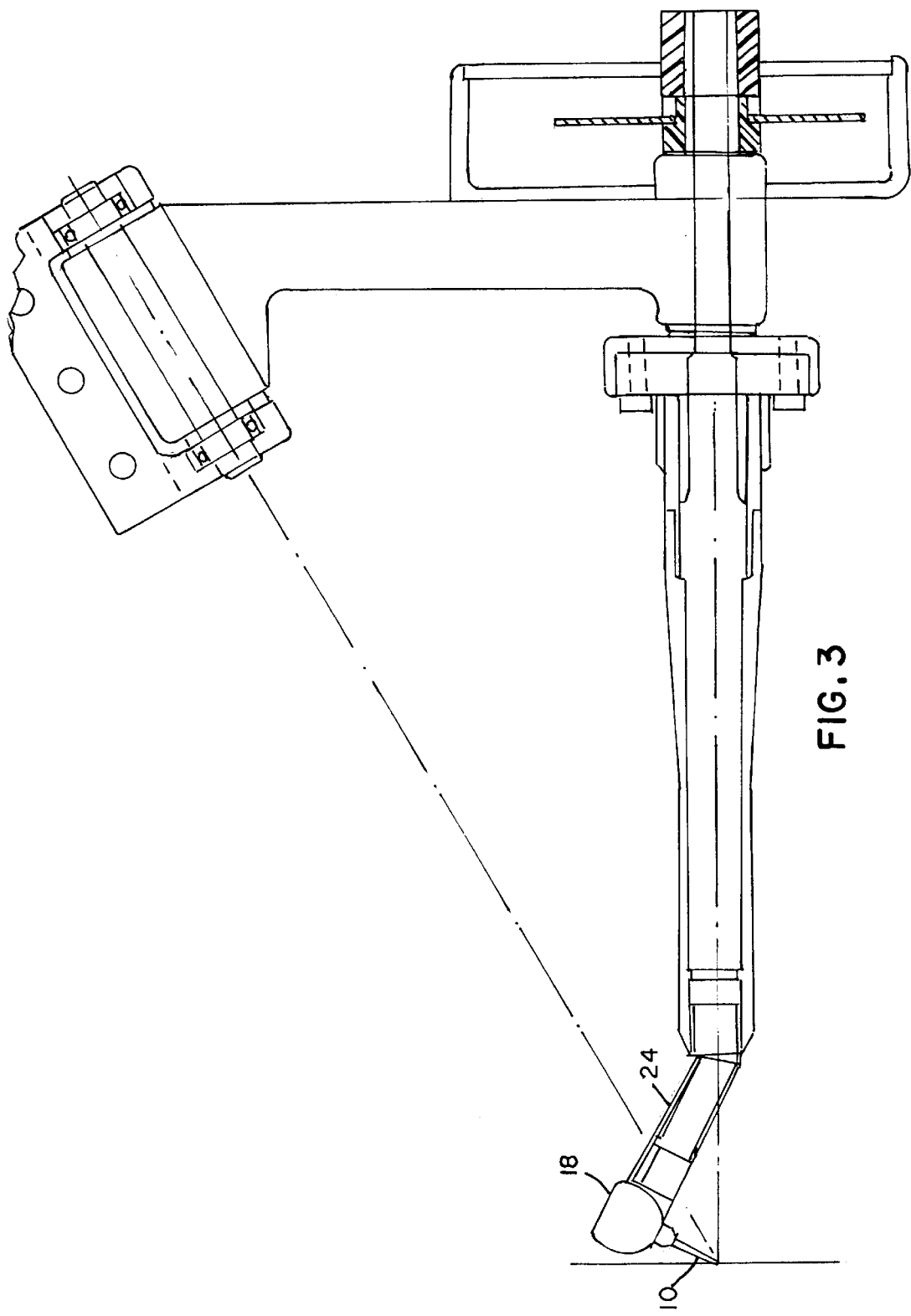
FIG. 3 is a side elevational view, partially in section, of the stylus, main arm and holding arm of the present invention.

Referring now to the drawings in detail, and particularly to FIG. 1, there is shown a method and a system for the remote sensing of a body component by a hand held moveable stylus which permits the simultaneous recordation of a plurality of signals to map and track the shape, size, and contour of a component "C", such as a body organ, i.e., a tooth, bone, or the like. The system includes a stylus 10, which is an elongated pin 12 pivotably supported along its mid portion 14, in a head 16. The distal end of the stylus 10 has a first radius. The second end of the stylus is movably supported within a hemispherically shaped electrode 18 in the head 16. A compression spring 20 maintains a bias on the stylus 10, yet permits the proximal end of the stylus 10 to pivot and strike the electrode 18 during a swinging or pivoting motion of the stylus 10 or a longitudinal motion of the stylus 10. When such contact is made, a signal is sent through a proper circuit, not shown for clarity, for recordation as to the time and the location of such contact.

The stylus 10 and head 16 are disposed on the distal end of a freely swingable first arm 24. The first arm 24 is supported on a main shaft 26. The first arm 24 is permitted to swing or pivot in any direction or angle because the main shaft 26 is rotatably supported in a bearing 28 disposed on the distal end of a holding arm 30. The holding arm 30 is supported in a bearing 32 on the distal end of a second arm 34. The second arm 34 is supported by a bearing 36 having a vertically disposed axis "A". The vertically disposed axis holding the second arm 34 is always in vertical alignment with the distal (tip) end of the stylus 10. The second arm 34 is connected to an arrangement of parallelogram linkages 40, forming a 3-D pantograph. The pantograph is anchored to a support stand 42 or to ground. The rear end 60 of the pantograph linkage 40 is attached to a laser beam generator 46, as shown in FIGS. 1 and 4.

The laser beam generator 46 has an output, a proportion of which comprises a reflected beam and a straight exit beam. The exit beam and the reflected beam are directed towards X, Y, and Z planes of a sensor apparatus 50 as shown in FIG. 1. Such sensor apparatus 50 may be also seen in the aforementioned patents, incorporated by reference herein. Such a sensor is similar to that manufactured by EG&G called an Amorphous Silicon Screen Sensor.

The second arm 34, connected to the first vertical linkage G, comprises one side of the first parallelogram ABCG. The first vertical linkage G has an upper bearing and a lower bearing thereattached. An upper first horizontal linkage A and a lower first horizontal linkage C are attached to upper and lower portions of the first vertical linkage G by a bearing which permits the upper horizontal linkage A and the lower horizontal linkage C to move in a vertical plane. A second vertical linkage B completes the first rectangle ABCG comprising the pantograph. The second vertical linkage B has a bearing on its uppermost end, in arrangement with the first horizontal linkage and the lower horizontal linkage. The second vertical linkage B also has an upper and a lower bearing permitting rotation of that vertical linkage about the vertical axis. A second parallelogram AA, BB, CC and DD comprised of a second primary vertical linkage DD, each second primary vertical linkage and second secondary vertical linkage are connected by parallel upper and lower linkages. The first parallelogram and the second parallelogram are each connected by a pair of upper and lower linkages E, EE and F, FF, one of which extends to a third vertical linkage "S" for ground support.

Figure 4:
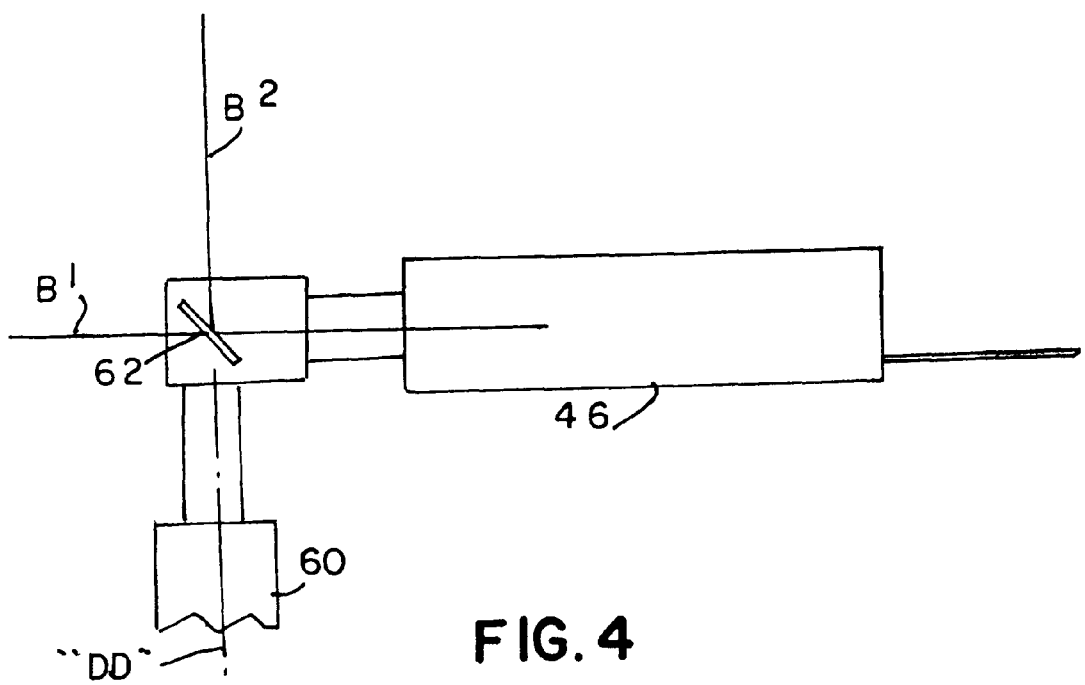
FIG. 4 is a side elevational view of a laser generator arrangement of the present invention.

The second primary vertical linkage DD has a upper end onto which a laser beam generator is mounted as shown in FIG. 4. The laser beam generator has a beam reflector 62 thereon. The laser beam "B" passes partially through the reflector and part of the beam $B^2$ is reflected by the reflector.

The axis of rotation of the second primary vertical linkage is coaxial with the reflected laser beam, reflected from the reflector. The reflected laser beam strikes the aforementioned sensor in the plane defined by the XY axes thereof. The exit beam passing through the reflector strikes the sensor defined by the ZX axes.

The split laser beam output permits simultaneous tracking by the sensors, of the motion by the stylus. When the stylus is in contact with an object, such occurance and location is recorded by virtue of the electrode input generated by its contact with the stylus head. The spherical contact area of the head is twice the radius of the stylus. By virtue of the relative sizes of the two parallelogram connected as the pantograph assembly, there is a proportion two to one ratio of motion to tracking dimension recorded by the sensor. The location of the distalmost tip of the stylus is always in axial alignment with the first vertical link of the first parallelogram, no matter what angle the stylus head is turned, rotated, or swung in, such orientation is always maintained. The reflected laser beam is always in axial alignment with the second primary vertical link of the second parallelogram. Thus the multiplication factor between the two parallelagrams in their pantograph linkages permits an accurate tracking of location and data through a proper control circuit connected to the sensors. By the combination of signals from the stylus, as to when contact is made with an article or object and its recordation through the circuit from the electrode in the head, in conjunction with the signals generated by the laser beam, an accurate domain may be mapped of a body component or the like.

We claim:

1. An arrangement for the remote sensing and recordation of information of a body component, comprising:

a stylus held within a support head, said support head having an electrode therein for the detection and recordation of stylus contact with a body component;

a plurality of parallelogram linkages articulably supporting said stylus, said linkages having a first or input end and a second or output end;

a motion tracking generator attached to said output end of linkages; and a sensor arranged to receive and record signals from said tracking generator in a plurality of orthogonal planes, so as to permit the generation and recordation of contours, location and domain of the body component being sensed by said stylus.

2. The arrangement for the remote sensing and recordation of a body component as recited in claim 1, wherein said tracking generator comprises a laser beam generator.

3. The arrangement for the remote sensing and recordation of a body component as recited in claim 2, wherein said parallelogram linkages includes a first linkage having an axis which is in axial alignment with the distal end of said stylus.

4. The arrangement for the remote sensing and recordation of a body component as recited in claim 2, wherein said parallelogram linkages has an end linkage with an axis which is in coaxial alignment with the axis of a beam generated by said laser generator.

5. A method of sensing and recordation of the contours and location of a body component using a plurality of pantograph linkages having a movable stylus an an arm at a first end of said linkages and a signal generator at a linkage at a second end of said linkages, comprising the steps of:

moving said stylus about and against the body component being sensed;

recording the location of said stylus during touching contact of said stylus with said body component; and generating an output signal by said signal generator attached to said second end of linkage, to track and permit the recording of the location of said stylus as said stylus is moved about said body component.

6. The method of sensing and recordation of the contours and location of a body component as recited in claim 5, including the step of:

receiving said output signal onto an XYZ plane sensor to permit the receipt and recordation of said output signals.

7. The method of sensing and recordation of the contours and location of a body component, as recited in claim 6, including the step of:

splitting said output signal onto a plurality of receiving sonsors screens to permit separation and identification of said signal.

* * * * *